United States Patent [19]

Michal

[11] Patent Number: 5,110,551

[45] Date of Patent: May 5, 1992

[54] ZERO DIFFUSION PATH GAS DOSIMETER SYSTEM AND METHOD

[75] Inventor: Jan Michal, Prague, Czechoslovakia

[73] Assignee: ORE Research Institute, Prague, Czechoslovakia

[21] Appl. No.: 637,115

[22] Filed: Jan. 3, 1991

[51] Int. Cl.$^5$ .................. G01N 21/00; G01N 31/22
[52] U.S. Cl. ........................................ 422/58; 422/56; 422/57; 422/86; 422/87; 422/88; 435/807; 436/167; 436/169; 436/902
[58] Field of Search ............... 436/122, 116, 167, 169, 436/902; 422/56, 57, 58, 86, 87, 88; 435/807

[56] References Cited

U.S. PATENT DOCUMENTS 4,092,120  5/1978  Souvaniemi .................. 422/58 X

Primary Examiner—Robert J. Warden
Assistant Examiner—Stephanie Blythe
Attorney, Agent, or Firm—M. K. Silverman

[57] ABSTRACT

A personal dosimeter for measuring the average concentration of undesirable contaminants gases such as nitrogen oxide includes a gas permeable web-like wafer formed of a material inert to polyamine. The wafer has a surface area having a numerical value at least one thousand times the value of the axial width of the wafer. The wafer is soaked in an absorptive medium not containing the ambient contaminant gas to be measured. The wafer, so soaked, is inserted within a gaseous impermeable housing from which the wafer may be selectively release and re-inserted. During an interval of release of the wafer, it is exposed for a predetermined interval of time to the ambient atmosphere. After re-insertion, the dosimeter is taken to an analysis site at which the wafer is removed and the molar concentration of products reaction with the atmospheric contaminant is measured.

7 Claims, 1 Drawing Sheet

ZERO DIFFUSION PATH GAS DOSIMETER SYSTEM AND METHOD

BACKGROUND OF THE INVENTION

The present invention relates to the field of gas monitoring and dosimetry in and, more particularly, to the field of passive dosimetry of hazardous gases, and concentration of ambient contaminants in the air.

Monitoring and sensing, also known as dosimetry, of hazardous gas concentrations is of considerable importance in the protection of employees of industrial plants and, more generally, the protection of civilian populations surrounding chemical operations and the protection of military personnel exposed to hazardous gas environments.

Numerous technologies have been developed for the estimation of what is term the time weighted average (TWA) gas concentration and for the estimation of gas exposure levels. The better known, and most important, of the existing methods of this type are briefly set forth below.
1. Bubbling of a known quantity of air through an absorbing solution and measuring concentrations of its reaction products in the solution.
2. Passing a known quantity of gas through a column with a solid adsorbent which either changes color or is de-absorbed in a subsequent step, with the quantity of the de-adsorbed gas being determined.
3. Adsorption of gas onto an activated carbon bed by means of a plastic material with apertures, and measuring the quantity of adsorbed gas over a known period of time.
4. Absorption of gas into a solution and measuring the concentration of its reaction products on a continual basis, for example, through the use of an electrochemical cell.
5. Measuring the change in electrical properties of surfaces of solid state devices after contaminant gases have been adsorbed by them.
6. Measuring the length of color-stain developed in an open-end tube filled with a chromophore.
7. Using a diffusion-barrier based passive sampler with a subsequent analysis employing spectrometric, electrochemical or chromatographic methods.

Commercially available gas dosimeters employing the techniques described above are generally designed for collecting ambient gas samples in the workplace and then, in a subsequent step, an employee-carried dosimeter is analyzed by an appropriate analytical method or instrument. Typically, each dosimeter is designed for a particular gas and, therefore, a different analytical method is required for each gas. Moreover, commercially available gas monitoring devices which employ the above methods are of high cost. Therefore, there has been, and currently exists, a need for economical gas monitoring techniques which is suitable to relatively wide range of gas monitoring situations.

The present invention is of a gas diffusion type and therefore, most closely resembles the prior art of Paragraph Number 3 above. More particularly, the present invention relates to a zero diffusion path gas dosimeter used in measuring the TWA gas concentration. An auxiliary instrument is contained within an enclosure adapted for selectable attachment and detachment to a worker which, both prior and subsequent to use is acted upon according to steps of the inventive method.

The prior art, as known to the inventor herein, is best reflected in U.S. Pat. Nos. 3,661,027 (1972) to Smith; U.S. Pat. No. 4,772,560 (1988) to Attar; and my own Czechoslovakia Patent No. 245,837.

The instant invention is also an improvement with respect to colormetric gas dosimeter reflected in U.S. Pat. Nos. 4,783,316 (1988) and 4,844,867 (1989) in which the measurement reaction products occurs within an instrument attached to the worker.

SUMMARY OF THE INVENTION

The invention defines a method of monitoring the TWA concentration of dangerous gases within the ambient atmosphere by means of a passive dosimeter, based upon the principle of diffusion gas flow. In accordance with the present invention, an insert consisting of a plurality of layers of web-like polymeric material is soaked in an absorptive substance of liquid polyamines such as triethanolamine. It is important that the insert be saturated by the absorptive medium in an environment which is known to be free of the gas to be monitored. As a second step, the soaked insert is placed within a protective housing having an exterior surface adapted in size and shape for attachment to the clothing of a worker. As a third step, when measurement of the ambient atmosphere is desired, the insert and its associated containment means is snap-fittably removed from said housing while the hosing remains attached to the clothing of a worker. Following exposure of the insert to the ambient atmosphere for a pre-determined interval of time, the insert and its associated frame, which is connected to said housing by a flexible integral member, is again closed. As a final step, the entire system is delivered to an analysis cite for assessment of the concentration of a reaction products of the gas to be measured using a well known method of colorimetry, which will vary with the gas to be monitored.

It is accordingly an object of the present invention to provide a personal use passive gas dosimeter method and related system that is simple in construction, easy to use and highly reliable.

It is another object of the present invention to provide a gas monitoring device which is inexpensive and disposable.

It is a further object of the to provide a passive dosimeter of gas diffusion type in which only an auxiliary element of the overall system need be wore upon the clothing of the user.

It is a yet further object to provide a passive dosimeter having essentially a zero length diffusion path in which a gaseous oxide in the ambient atmosphere is captured.

It is a still further object of the present invention to provide a physico-chemical system for the monitoring of gaseous oxides, such an nitrogen oxide and sulphur dioxide, in which the ambient matter is caught within a triethanolamine soaked polymeric net.

The above and yet other objects and advantages of the present invention will become apparent from the hereinafter set forth Brief Description of the Drawings, Detailed Description of the Invention, and Claims appended herewith.

The operation of prior art passive gas diffusion dosimeters is governed by a known equation of non-direct, isotheremal, isobaric diffusion of a gas 1 through the mixture of gases 1 and 2.

This equation is deducted from the first Fick Law which is as follows:

$$J = -D_{12} dc'/dz$$

Where J is the molecular flow of gas 1 D12 is the diffusion co-efficient of gas 1 by gas 2, C1 is the concentration of the gas 1 being diffused and Z is the length of diffusion in the direction of the diffusion flow.

From this equation, it can be deduced that the amount of matter entrained (caught) by an absorption medium during a unit of time is dependent on the relationship between the area of the absorption surface relative to the length of the diffusion zone (that is, the axial width) of the absorptive medium. According to this equation when there exist extremely low values of length in the direction of the diffusion path, the above equation breaks down in that J would approach infinity.

The above theoretical problems and practical disadvantages in prior art dosimeter gas diffusion are eliminated in the present inventive personal dosimeter and, as such, the above general equation is not applicable.

Figure 1:
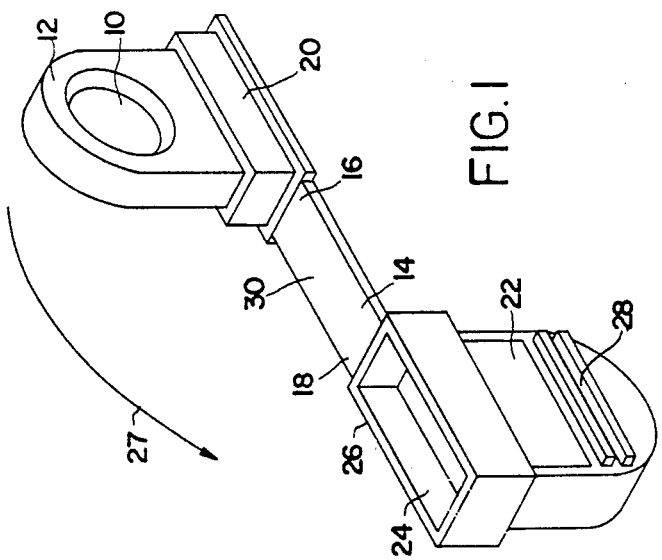
FIG. 1 is a perspective view of a first embodiment of the inventive dosimeter.
Figure 2:
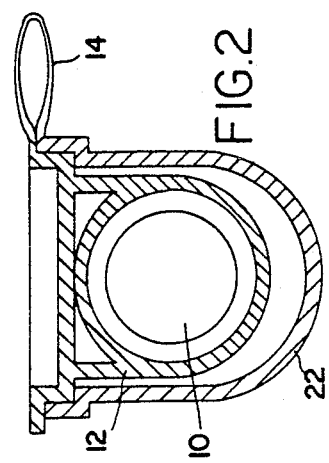
FIG. 2 is a radial cross-sectional view of the dosimeter showing the device of FIG. 1 when fully assembled.

With reference to FIGS. 1 and 2, the instant invention is seen to include a gas permeable web-like wafer 10 formed of a material that is inert to polyamines that, more specifically, is inert to a mixture of clear triethanolamine and acetone, more fully described below.

Further provided is a frame 12 which is secured circumferentially about said wafer 10. Also provided is a flexible elongated member 14 having first and second ends 16 and 18 respectively. Said member 14 is integrally formed, at said first end 16 thereof, with a surface 20 of said frame 12.

As may be further noted in the views of FIGS. 1 and 2, there is yet further provided a gas impermeable housing 22 which is proportioned for close enclosure about said frame 12. Said housing 22 exhibits a mouth 24 proportioned for securable receipt of said frame 12. It is noted that said mouth 24 is, at a side 26 thereof, integrally connected with said second end 18 of said flexible member 14.

The overall effect and operation of the above described structure is that said frame 12 and wafer 10 secured therein may be selectably inserted (see path of arrow 27) into said gas in permeable housing 22 after wafer 10 has been soaked within said absorptive polyamine mixture and, after storage, may, as by finger tip engagement of said surface 20 with one hand and finger engagement of ridges 28 of housing 22 with the other hand, be selectably released from the housing when a user of the system wishes to expose the soaked wafer 10 to an ambient atmosphere for an interval of time for purposes of measuring the TWA of a specific contaminant gas in the ambient atmosphere. After such interval of time has elapsed, wafer 10 and its associated frame 12 may be readily re-inserted into housing 22, to achieve the structure shown in FIG. 2. Thereafter, the entire assembly may be transported to a site at which appropriate physico-chemical analytic equipment with which the products of the reaction between the monitored gas and the polyamine soaked wafer may be quantitatively determined. That is, the number of grams of the product of such reaction being directly related to the TWA of the monitored gas.

With respect to the physical characteristics of gas permeable wafer 10, it will, typically, comprise a polymeric web having an axial width of less than one millimeter. Further, it has been found suitable to make use of a plurality of such webs having, in aggregate, an axial width not exceeding one millimeter. Suitable materials from which the polymeric web may be formed include polyethylene and polypropylene. The radial surface area of wafer 10 which is optimal for effective absorption is in the range of one to two cubic centimeters. Accordingly, the ratio of the numerical value of the surface (quadratic) area of wafer 10 to its width is in the range of 1000:1 to 2000:1. The term zero diffusion length and/or substantially zero diffusion length as used in this specification should be understood to constitute an absorptive medium in which the numerical value of the absorptive surface area is at least one thousand times greater than the diffusion path.

Prior to usage, said gas permeable wafer 10 must be soaked in a mixture of polyamines and, preferably, a mixture in the ratio of three-to-one of clear triethanolamine and acetone until the wafer has been thoroughly soaked, which typically will take about fifteen minutes. The wafer is then dried for about fifteen minutes in an uncontaminated atmosphere. This results in the evaporation of the acetone.

The wafer is then inserted into the frame 10. Thereafter, surface 20 and associated flexible member 14 may be press-fittably inserted into mouth 24 and into housing 22 such that wafer 10 and frame 12 are sealed within the housing 22 in the manner shown in FIG. 2.

The assembly consisting of wafer 10 and frame 12 is selectably released from housing 22 when an user wishes to monitor, for a given interval of time, concentration of a gas, such as nitrogen oxide or sulphur dioxide, with which the polyamine media within which wafer 10 has been soaked is reactive. While the dosimeter types shown in FIGS. 1 and 2 is secured to the user, the exposure of the wafer 10 occurs. Such securement may be accomplished by any number of securement means. For example, in FIG. 1, there is shown a hole 30 which enables the system of FIG. 1 to be attached to the clothing of a worker through the use of safety pin or the like. Alternatively, exterior surfaces of housing 22 may be provided with VELCRO means complemental to VELCRO means provided upon the clothing of the worker such that housing 22 may be press-fittably attached to the worker's clothing thereby permitting the suspension of frame 12 via flexible member 14.

After the pre-determined interval of gas contaminant measurement has elapsed, the dosimeter is returned to the position of FIG. 2, that is, wafer 10 and associated frame 12 is re-inserted into housing 22. Thereafter, at a time convenient to the worker, the entire unit is brought to an analysis site at which location wafer 10 can be removed from frame 12. Thereby, the number of grams of material produced as a product of the reaction between the monitored gas and the polyamine solution can be measured and, through appropriate correlation, the time waited average TWA gas concentration for the gaseous contaminant of interest can be derived.

Figure 3:
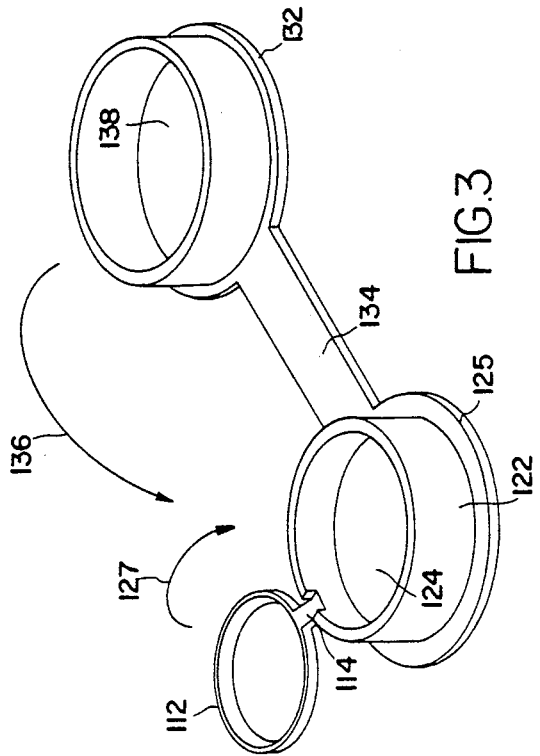
FIG. 3 is a perspective view of a second embodiment of the invention.
Figure 4:
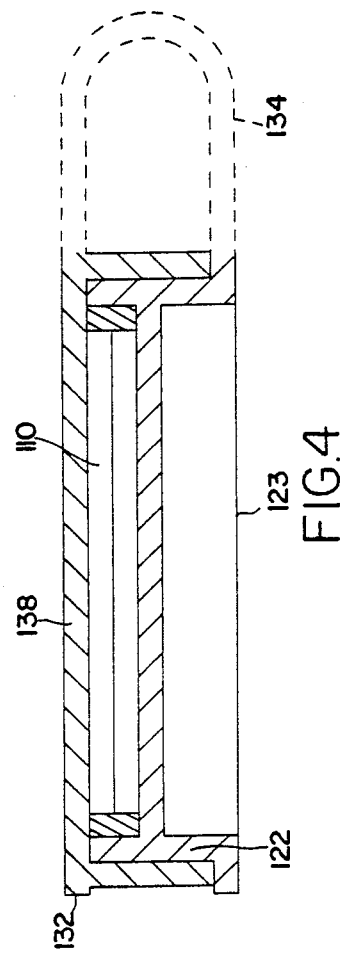
FIG. 4 is an axial cross-sectional view of the embodiment of FIG. 3 when fully assembled.

A further embodiment of the invention is shown in FIGS. 3 and 4. Therein, a wafer 110 is surrounded by a frame 112 in the manner above described with reference to elements 10 and 12 shown in FIGS. 1 and 2.

With further reference to FIGS. 3 and 4, there is shown a hollow substantially rigid cylindrical housing 122 having a base 123 which includes annular shoulder 125. Housing 122 is connected to frame 112 by flexible member 114. In much the manner above described in the embodiment of FIGS. 1 and 2, frame 112 may be selectively secured within mouth 124 of housing 122 through the rotation of frame 112 in the direction indicated by arrow 127.

Further shown in FIGS. 3 and 4 is a circumferential measuring means 132 which is connected to said housing 122 by flexible member 134. Rotation of said means 132 in the direction shown by arrow 136 occurs after frame 112 has been rotated onto mouth 124 of housing 122. Integral base 138 of housing means 132 will assure the fluid integrity of the resulting system which is shown in FIG. 4. Then, wafer 112 will be secured within frame 112 which in turn is secured within mouth 124 of housing 122. Above frame 112 will be base 138 of circumferential housing means 132 and, as well, the entire structure will be sealed by the axial walls of housing 132. The overall effect and operation of the embodiment of FIGS. 3 and 4 is similar to that of the embodiment of FIGS. 1 and 2.

Accordingly, while there has been shown and described the preferred embodiment of the instant invention (the embodiment of FIGS. 1 and 2), it is to be understood that the invention may be embodied otherwise than is herein specifically illustrated and described and that, within said embodiment, certain changes in the details of construction and in the form and arrangement of the parts may be made without departing from the underlying idea or principles of this invention within the scope of the claims appended herewith.

Having thus described my invention, what I claim as new, useful and non-obvious and, accordingly, secure by Letters Patent of the United States is:

1. A personal gas diffusion dosimeter, comprising:

(a) a gas permeable wafer formed of a material that is inert to polyamine, said wafer formed of a polymeric web having an axial gas diffusion length of substantially zero;

(b) a circumferential frame securably holding said wafer;

(c) a flexible elongate member having first and second ends, integrally formed at said first end thereof with a surface of said frame; and (d) a rigid gas impermeable housing proportioned for enclosure about said frame, said housing having a mouth proportioned for securable receipt of said frame, said mouth, at a side thereof, integrally connected with said second end of said flexible member, whereby said wafer-holding frame may be selectably inserted into said housing, after soakage of the wafer within an absorptive medium, and may be selectably released from said housing when a user wishes to expose the soaked wafer to an ambient atmosphere for an interval of time, and may be re-inserted into said housing after said interval has elapsed.

2. The dosimeter as recited in claim 1 in which said wafer comprises a plurality of wafers.

3. The dosimeter as recited in claim 1 in which said wafer has a radial surface area between one and two cubic centimeters and a width of less than one millimeter.

4. The dosimeter as recited in claim 1 in which the material of said polymeric web is selected from the group consisting essentially of polyethylene and polypropylene.

5. The dosimeter recited in claim 1, further comprising selectable fastening means secured upon an exterior surface of said housing.

6. The dosimeter as recited in claim 5 in which said fastening means comprises VELCRO means.

7. The dosimeter as recited in claim 1 in which the numerical value of the radial surface area of said wafer is at least 1000 times the numerical value of the width of said wafer.

* * * * *